United States Patent [19]

Evans et al.

[11] Patent Number: 5,668,175

[45] Date of Patent: Sep. 16, 1997

[54] USE OF SELECTIVE LIGANDS FOR TREATMENT OF DISEASE STATES RESPONSIVE TO STEROID OR STEROID-LIKE RETINOIDS

[75] Inventors: Ronald M. Evans, La Jolla; Richard A. Heyman, Encinitas; Christina S. Berger; Robert B. Stein, both of San Diego, all of Calif.

[73] Assignee: The Salk Institute for Biological Studies, La Jolla, Calif.

[21] Appl. No.: 695,743

[22] Filed: Aug. 12, 1996

Related U.S. Application Data

[63] Continuation of Ser. No. 193,146, filed as PCT/US92/07064, Aug. 2, 1992 published as WO93/03713, Mar. 4, 1993, abandoned, which is a continuation-in-part of Ser. No. 748,767, Aug. 23, 1991, abandoned.

[51] Int. Cl.$^6$ .......................... A61K 31/19; A61K 31/165
[52] U.S. Cl. ............................... 514/569; 514/617
[58] Field of Search ....................... 514/569, 617

[56] References Cited

FOREIGN PATENT DOCUMENTS

| 0 170 105 | 2/1986 | European Pat. Off. . |
| 0 220 118 | 4/1987 | European Pat. Off. . |

OTHER PUBLICATIONS

Astrom et al., "Retinoic Acid And Synthetic Analogs Differentially Activate Retinoic Acid Receptor Dependent Transcription", *Biochemical and Biophysical Research Communications* 173(1): 339–345 (1990).

Crettaz et al., "Liquid specificities of recombinant retinoic acid receptors RARα and RARβ", *The Biochemical Journal* 272(2):391–397 (1990).

Delescluse et al., "Selective High Affinity Retinoic Acid Receptor α or β–γ Ligands", *Molecular Pharmacology* 40(4):556–562 (1991).

Frey et al., "Antiproliferative activity of retinoids, interferon α and their combination in five human transformed cell lines", *Cancer Letters* 57:223–227 (1991).

Graupner et al., "6'–Substituted Naphthalene–2–Carboxylic Acid Analogs, A New Class Of Retinoic Acid Receptor Subtype–Specific Ligands" *Biochemical and Biophysical Research Communications* 179(3):1554–1561 (1991).

Kagechka et al., "Differentiation Inducers of Human Promyelocytic Leukemia Cells HL–60'" *Chem. Pharm. Bull.* 34(5):2275–2278 (1986).

Kakizuka et al., "Molecular Cloning and Characterization of Aberrant Retinoic Acid Receptors From A t(15;17) Positive Acute Promyelocytic Leukemia Patient", *Journal of Cellular Biochemistry* vol. Supplement No. 15G, p. 31 (Apr. 1991).

Lehmann et al., "Identification of Retinoids with Nuclear Receptor Subtype–selective Activities", *Cancer Research* 51:4804–4809 (1991).

Reynolds, J.E.F., "Martindale The Extra Pharmacopoeia" *The Pharmaceutical Press,* London, Acitretin, p. 916 (1989).

*Primary Examiner*—Kimberly Jordan
*Attorney, Agent, or Firm*—Gray Cary Ware & Freidenrich; Stephen E. Reiter

[57] ABSTRACT

In accordance with the present invention, there is provided a method for the treatment of subjects afflicted with steroid or steroid-like hormone-responsive disease states. The invention method comprises administering to the subject an effective amount of a ligand which selectively interacts with the receptor subtype associated with the steroid or steroid-like hormone-responsive disease state, wherein said ligand interacts with said receptor subtype to a significantly greater extent than with other subtypes of the same receptor class.

5 Claims, 5 Drawing Sheets

USE OF SELECTIVE LIGANDS FOR TREATMENT OF DISEASE STATES RESPONSIVE TO STEROID OR STEROID-LIKE RETINOIDS

RELATED APPLICATIONS

This application is a continuation application of U.S. Ser. No. 08/193,146, filed Feb. 14, 1994, now abandoned, which is in turn a 371 of PCT/US92/07064, filed Aug. 21, 1992, published as WO93/03713, Mar. 4, 1993, which is a continuation-in-part application of U.S. Ser. No. 07/748,767, filed Aug. 23, 1991, now abandoned, the entire contents of each of which are hereby incorporated by reference herein.

FIELD OF THE INVENTION

The present invention relates to therapeutic uses of compounds which function as steroid hormones or steroid-like hormones. In a particular aspect, the present invention relates to the use of compounds which selectively or preferentially interact with a single subtype of a given steroid hormone or steroid-like hormone receptor class.

BACKGROUND OF THE INVENTION

Many disease states are consistently associated with the occurrence of karyotypic change, e.g., a chromosomal translocation. For example, when the gene encoding PML (for "promyelocytes") undergoes a translocation with the retinoic acid receptor-α (RAR-α) (i.e., translocation between chromosomes 15 and 17 at the RAR-α and PML loci), the translocation is manifested as a form of leukemia, acute promyelocytic leukemia (APL).

It is possible, and even likely in many cases, that when translocation occurs, a gene product not normally subject to hormone expression control (e.g., PML) may be placed under the control of a hormone responsive sequence (e.g., RAR-α). Thus a gene such as PML may fall under the control of a hormone responsive sequence (such as RAR-α) as a result of a translocation event.

It has recently been discovered that APL can be effectively controlled by treatment with retinoic acid. Unfortunately, since several different receptors (and subtypes thereof) are known which respond to retinoic acid (e.g., RAR-α, RAR-β, RAR-γ, RXR-α, RXR-β, RXR-γ), administration of retinoic acid as a treatment for APL has the potential to cause many undesirable side-reactions for the patient.

There are numerous other disease states which have also been found to be responsive to treatment with hormones and/or hormone-like compounds. For example, Vitamin D-dependent Ricketts is responsive to treatment with Vitamin D, acne is responsive to treatment with retinoic acid, and the like. While available hormone or hormone-like compounds are effective for the treatment of such disease states, there is always the competing concern of undesirable side effects of such hormone treatments.

Accordingly, such disease states can potentially be much more effectively treated by using ligands which are selective for the specific receptor subtype which is involved in the disease state. Indeed, in view of the potential for the use of hormone therapy in the treatment of many disease states, it would be desirable to have the ability to selectively treat subjects with compounds which selectively interact as ligands with the specific receptor subtype involved in the disease state.

BRIEF DESCRIPTION OF THE INVENTION

In accordance with the present invention, we have discovered various compounds which selectively interact with a single receptor subtype, to a much greater extent than than do other subtypes of the same receptor class.

Such compounds are useful for the selective treatment of hormone responsive disease states, thereby minimizing the occurrence of side effects caused by the activation of hormone responsive pathways not directly associated with the disease state being treated.

DETAILED DESCRIPTION OF THE INVENTION

Figure 1:
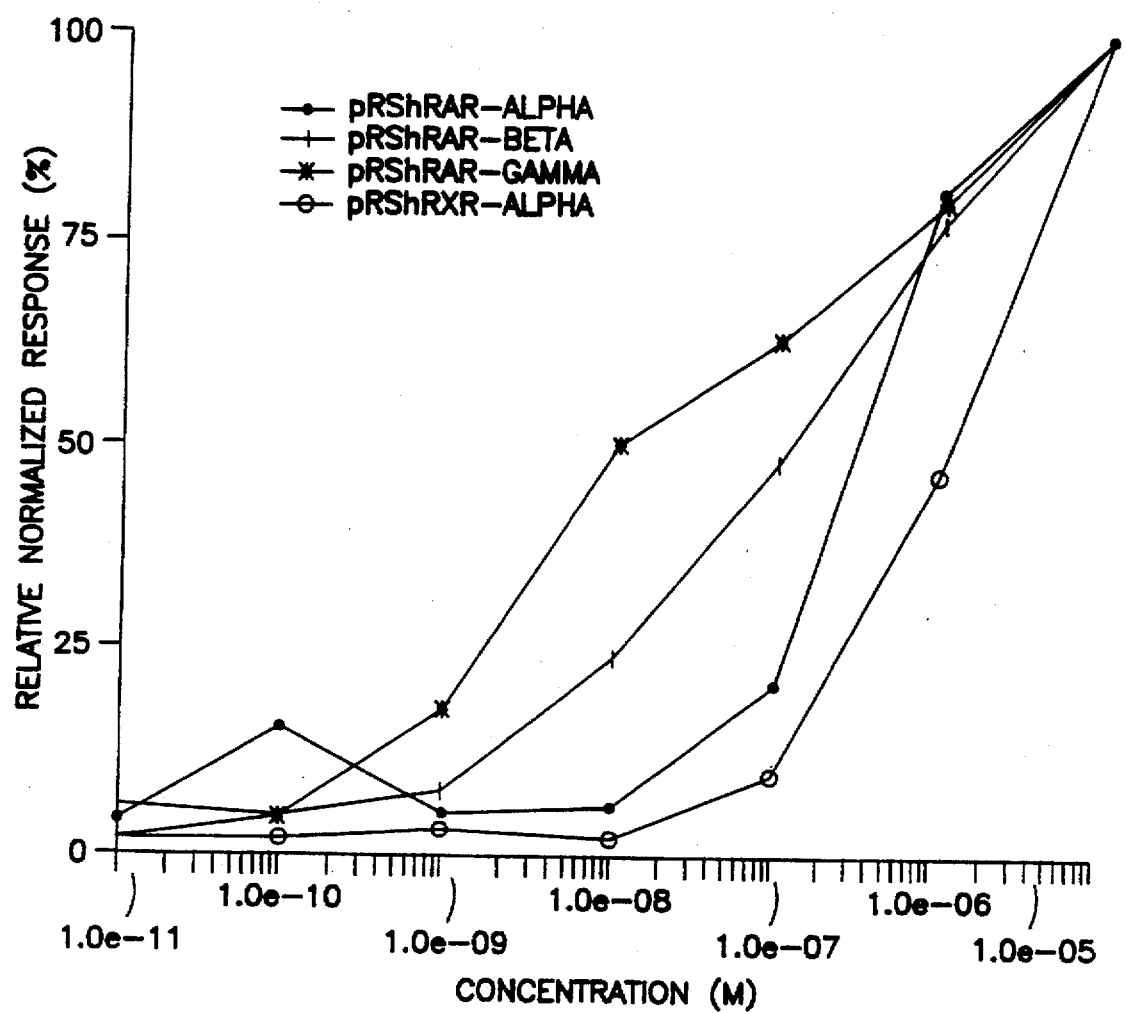
FIG. 1 is a dose response curve showing the response of RAR-α, RAR-β, RAR-γ, and RXR-α to increasing concentrations of retinoic acid.

In accordance with the present invention, there are provided methods for the treatment of a subject afflicted with a steroid or steroid-like hormone-responsive disease state, said method comprising administering to said subject an effective amount of a ligand which selectively interacts with the steroid or steroid-like hormone receptor subtype associated with said steroid or steroid-like hormone-responsive disease state, wherein said ligand selectively interacts with said steroid or steroid-like hormone receptor subtype associated with said steroid or steroid-like hormone-responsive disease state, to a significantly greater extent than do other subtypes of the same receptor class.

As employed herein, the phrase "steroid or steroid-like hormone-responsive disease state" refers to:

(i) any disease state wherein a gene product (or a portion of a gene product) not normally subject to steroid or steroid-like hormone expression control is placed, by translocation, under the control of a steroid or steroid-like hormone responsive sequence, or (ii) any disease state wherein a first gene product (or a portion of a gene product) subject to steroid or steroid-like hormone expression control by a first steroid or steroid-like hormone is placed, by translocation, under the control of a second steroid or steroid-like hormone responsive sequence, or (iii) any disease state which correlates with the expression of abnormal gene product, wherein said gene product (or a portion of said gene product) is normally subject to steroid or steroid-like hormone expression control, or (iv) any disease state which correlates with an abnormal level of expression of gene product, the expression of which is normally maintained under steroid or steroid-like hormone expression control, or (v) any disease state which correlates with an abnormal level of receptor, the presence of which is normally maintained under steroid or steroid-like hormone expression control, or (vi) any disease state which correlates with an abnormal level of ligand, the presence of which is normally maintained under steroid or steroid-like hormone expression control.

As employed herein, the phrase "ligand which selectively interacts with the receptor subtype associated with said steroid or steroid-like hormone responsive disease state to a significantly greater extent than with other subtypes of the same receptor class" refers to compounds which are preferentially selective for one receptor subtype in modulating the transcription activation properties thereof. The terminology "significantly greater extent", as applied to interaction between ligand and a specific receptor subtype, refers to ligands which have a significantly higher therapeutic index (i.e., the ratio of efficacy to toxicity) for treatment of the target disease state than for activation of pathways mediated by other subtypes of the same receptor class. The toxicity of therapeutic compounds frequently arises from the non-selective interaction of the therapeutic compound with receptor subtypes other than the desired receptor subtype. Thus, the present invention provides a means to dramatically reduce the incidence of side-reactions commonly associated with hormone therapy. See, for example, the selectivity demonstrated in FIGS. 2–5.

It is useful to distinguish the terms receptor "subtype" and receptor "class". For example, retinoid responsive receptors comprise a "class" of receptors, all of which are responsive to retinoid compounds. Similarly, thyroid hormone receptors comprise a "class" of receptors which are responsive to thyroid hormone. Each class can be divided into various subtypes, i.e., specific members of the class which have different tissue distributions, different affinities for the native ligand, different activation properties when contacted with the native ligand, and so on.

Some classes of receptors include sub-families of distinctly different types of receptors. Thus, for example, while the retinoid class of receptors includes both the retinoic acid receptors (RARs) and the retinoid X receptors (RXRs), these two different sub-families are clearly distinct. For example, each member of the RAR sub-family is responsive to a defined first hormone response element (HRE), and each member of the RXR sub-family is responsive to a defined second HRE (which is distinctly different from the first HRE). Accordingly, in accordance with the present invention, there are provided compounds which distinguish between the various sub-families of a receptor, and/or distinguish between the various subtypes thereof.

Ligands contemplated by the present invention are selected from RAR-α selective ligands, RAR-β selective ligands, RAR-γ selective ligands, TR-α-selective ligands, TR-β-selective ligands, RXR-α selective ligands, RXR-β selective ligands, RXR-γ selective ligands, coup-α selective ligands, coup-β selective ligands, coup-γ selective ligands, and the like.

Exemplary selective ligands contemplated for use in the practice of the present invention include the phenyl-naphthyl derivative having the structure:

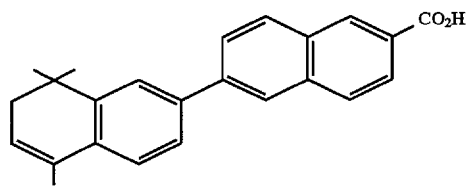

referred to herein as Compound I, which selectively interacts with the retinoic acid receptor-β and retinoic acid receptor-γ (see, for example, FIG. 2); the polyunsaturated carboxylic acid derivative having the structure:

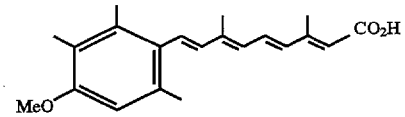

referred to herein as Compound II, which selectively interacts with RAR subtypes relative to RXR subtypes (see, for example, FIG. 3); the amide having the structure:

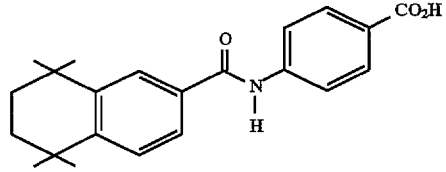

referred to herein as Compound III, which selectively interacts with RAR-α, and displays a different rank order of potency relative to the other RAR subtypes and RXR-α, relative to the other retinoid compounds tested (see, for example, FIG. 4); the benzophenone derivative having the structure:

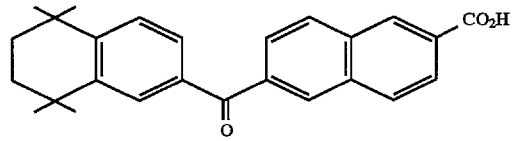

referred to herein as Compound IV, which selectively interacts with the retinoic acid receptor-β and retinoic acid receptor-α (see, for example, FIG. 5), and the like. These and many other compounds useful in the practice of the present invention are described in detail in *Chemistry and Biology of Synthetic Retinoids*, Dawson and Okamura, editors, CRC Press, Inc. (Boca Raton, Fla. 1990), incorporated by reference herein.

The above-described ligands, in suitable form (employing suitable vehicle for delivery, such as, for example, gelatin capsule(s) or compressed tablet(s) where oral administration is contemplated; in an appropriate base where topical administration is contemplated; in a suitable infusion medium where injection or other means of delivery are contemplated; and the like), can be administered to a subject employing standard methods, such as, for example, orally, topically (e.g., transdermal mode of administration), by intraperitoneal, intramuscular, intravenous, or subcutaneous injection or implant, and the like. One of skill in the art can readily determine appropriate dosage(s), treatment regimens, etc. depending on the mode of administration employed.

For example, for oral administration, dosages in the range of about 1 up to 500 mg/kg body weight per day, depending on the disease state being treated, will be employed. Active compound can be administered in a sustained release form, or in divided doses throughout the day. For topical delivery, in the range of about 0.05 mg up to 10 mg/kg body weight per day, depending on the disease state being treated, will be employed. For injection modes of delivery, in the range of about 10 µg up to 2 mg/kg body weight per day, depending on the disease state being treated, will be employed. It should be emphasized, however, that dosage requirements are variable and are typically individualized on the basis of the disease under treatment and the response of the patient. After a favorable response is noted, the proper maintenance dosage can be determined by decreasing the initial drug dosage in small increments at appropriate time intervals until the lowest drug dosage which will maintain an adequate clinical response is reached. Those of skill in the art recognize that constant monitoring of the patient's condition is desirable in regards to drug dosage.

In accordance with a particular embodiment of the present invention, there is provided a method for the treatment of a subject afflicted with acute promyelocytic leukemia, said method comprising administering to said subject an effective amount of a ligand which selectively interacts with retinoic acid receptors, in preference to retinoid X receptors. In a preferred embodiment of the present invention, an effective amount of a ligand which selectively interacts with RAR-α, relative to other retinoic acid receptor subtypes (as well as retinoid X receptors), will be employed. Ultimately, physicians will determine the particular dosage of the selective ligand which is most suitable. The selected dosage will vary depending upon the mode of administration employed, the particular compound administered, the patient under treatment, and the particular disease being treated.

In addition to the above-described applications of the invention treatment method, the method of the invention can be applied to the selective treatment of skin disorders such as acne, psoriasis, photodamage, and the like. For such applications, compounds which selectively interact with RAR-α, relative to other retinoid receptors, are preferred.

It can be readily seen, therefore, that the invention treatment method is useful in the treatment of a wide variety of disease states.

The invention will now be described in greater detail by reference to the following non-limiting examples.

EXAMPLES

A series of dose response curves were generated to determine the response of retinoic acid receptor-α, retinoic acid receptor-β, retinoic acid receptor-γ and retinoid X receptor-α upon exposure to retinoic acid, Compound I (i.e., the phenyl-naphthyl derivative), Compound II (i.e., the polyunsaturated carboxylic acid derivative), and Compound III (i.e., the amide derivative), and Compound IV (i.e., the benzophenone derivative).

Response to the various compounds was measured employing the "cis/trans assay" as described by Evans et al., in U.S. Ser. No. 108,471 (filed Nov. 30, 1988), the entire contents of which are hereby incorporated by reference herein. All assays were carried out employing CV-1 host cells co-transformed with vectors encoding a receptor selected from RAR-α, RAR-β, RAR-γ, or RXR-α and a reporter vector.

The retinoic acid receptor-α was encoded by vector pRShRAR-alpha (see U.S. Pat. No. 4,981,784, issued Jan. 1, 1991, the entire contents of which are hereby incorporated by reference herein), retinoic acid receptor-β was encoded by vector pRShRAR-beta (see Brand et al. in Nature 332:850 (1988) and Benbrook et al. in Nature 333:669 (1988), the entire contents of which are hereby incorporated by reference herein), retinoic acid receptor-γ was encoded by vector pRShRAR-gamma (see U.S. Ser. No. 370,407, filed Jun. 22, 1989, the entire contents of which are hereby incorporated by reference herein), and retinoid X receptor-α was encoded by vector pRShRXR-alpha (see U.S. Ser. No. 478,071, filed Feb. 9, 1990, the entire contents of which are hereby incorporated by reference herein).

The reporter vector used in all experiments was TREp-ΔMTV-LUC, as described by Umesono et al. in Nature 336:262 (1988), the entire contents of which are hereby incorporated by reference herein.

EXAMPLE I

Retinoic Acid Dose Response Curve

FIG. 1 presents the results of a dose response study carried out with retinoic acid as the ligand for each of the receptors: RAR-α, RAR-β, RAR-γ, and RXR-α.

At very low concentrations of retinoic acid (i.e., concentrations below about $1\times10^{-9}$), each of the retinoid receptor subtypes is activated to approximately the same extent. Similarly, at concentrations above about $1\times10^{-6}$, each of the retinoid receptor subtypes is activated to approximately the same extent. Although, in the concentration range of about $1\times10^{-9}$–$1\times10^{-6}$, there is a readily discerned rank order potency as follows:

RAR-γ>RAR-β>RAR-α>RXR-α, retinoic acid is seen to exert a substantial effect on each of the retinoid receptors tested. Administration of retinoic acid as a therapeutic agent is, therefore, likely to induce many hormone mediated pathways, not just the pathway involved in the disease state to be treated.

EXAMPLE II

Dose Response Curve For Compound I

Figure 2:
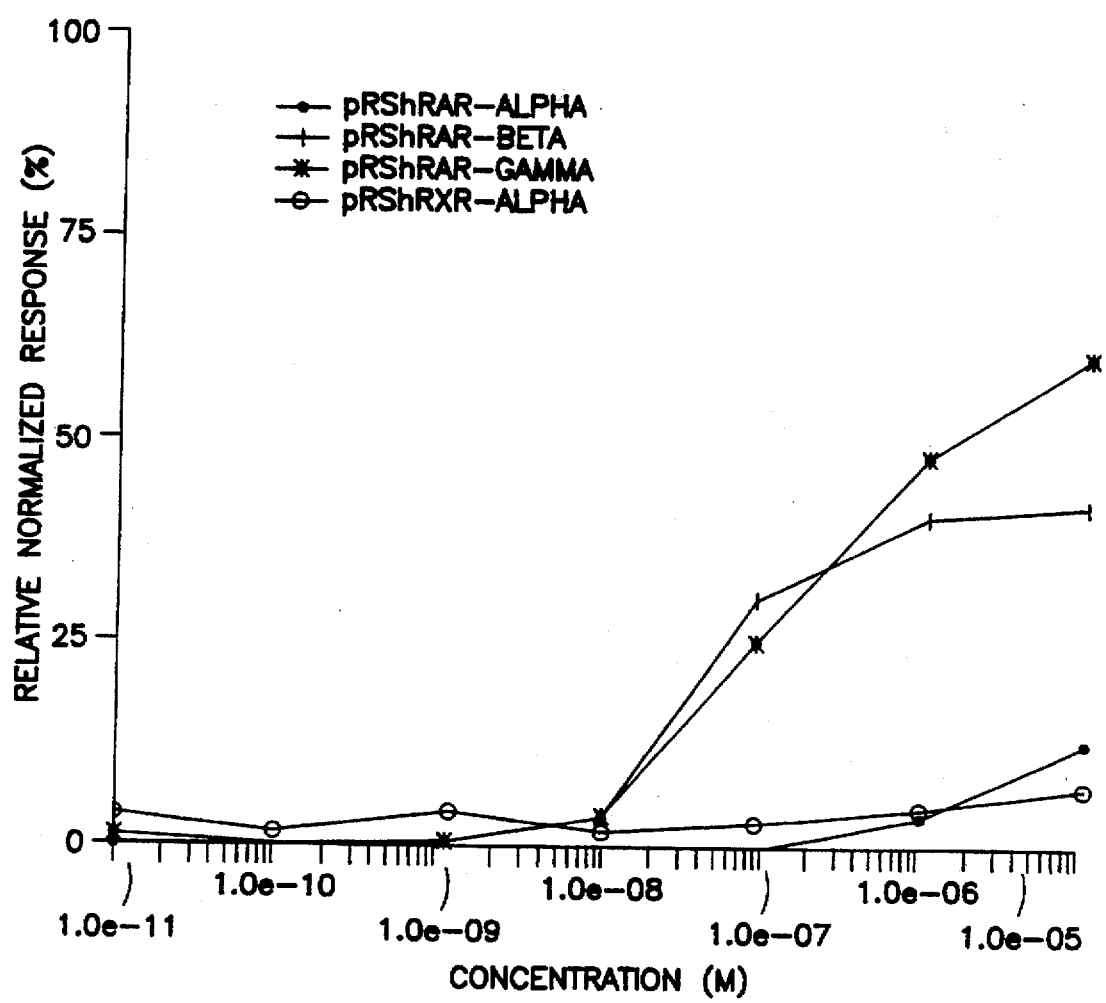
FIG. 2 is a dose response curve showing the response of RAR-α, RAR-β, RAR-γ, and RXR-α to increasing concentrations of the phenyl-naphthyl derivative referred to herein as Compound I.
Figure 2:
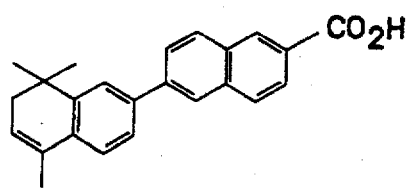

FIG. 2 presents the results of a dose response study carried out with Compound I (phenyl-naphthyl derivative) as the ligand for each of the receptors: RAR-α, RAR-β, RAR-γ, and RXR-α.

At very low concentrations of Compound I (i.e., concentrations below about $1\times10^{-8}$), each of the retinoid receptor subtypes is activated to approximately the same extent. However, at concentrations above about $1\times10^{-8}$, there is a readily discerned rank order potency as follows:

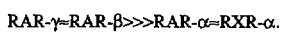

RAR-γ=RAR-β>>>RAR-α=RXR-α.

Thus, Compound I could be used for the treatment of a disease state which involves RAR-γ and/or RAR-β, without perturbing pathways which are responsive to RAR-α or the retinoid X receptor.

EXAMPLE III

Dose Response Curve For Compound II

Figure 3:
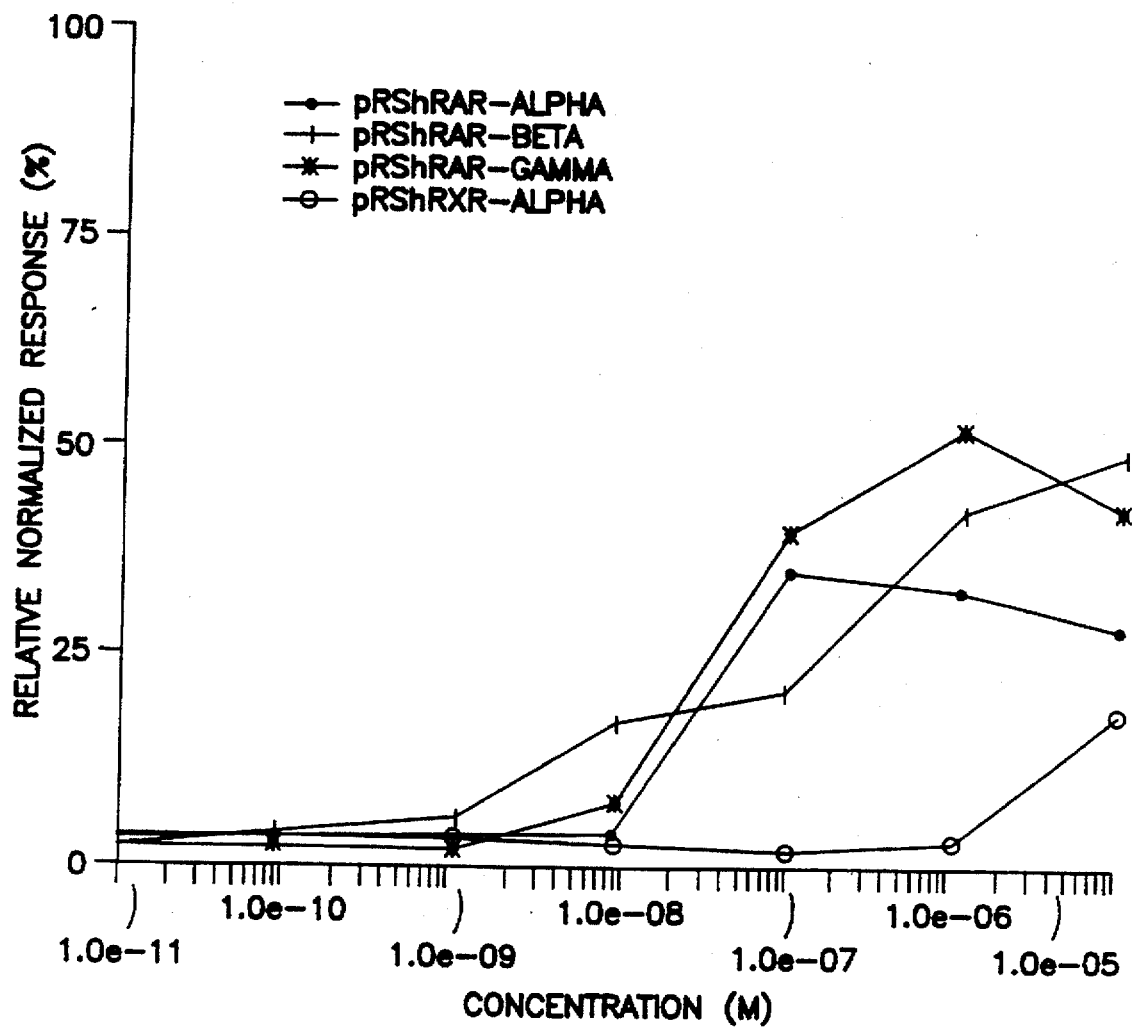
FIG. 3 is a dose response curve showing the response of RAR-α, RAR-β, RAR-γ, and RXR-α to increasing concentrations of the polyunsaturated carboxylic acid derivative referred to herein as Compound II.

FIG. 3 presents the results of a dose response study carried out with Compound II (polyunsaturated carboxylic acid derivative) as the ligand for each of the receptors: RAR-α, RAR-β, RAR-γ, and RXR-α.

At very low concentrations of Compound II (i.e., concentrations below about $1 \times 10^{-9}$), each of the receptor subtypes is activated to approximately the same extent. However, at concentrations above about $1 \times 10-8$, the rank order potency is as follows:

RAR-γ≈RAR-β≈RAR-α>>RXR-α.

Thus, Compound II could be used for the treatment of a disease state which involves a retinoic acid receptor, without perturbing pathways which are responsive to the retinoid X receptor.

EXAMPLE IV

Dose Response Curve For Compound III

Figure 4:
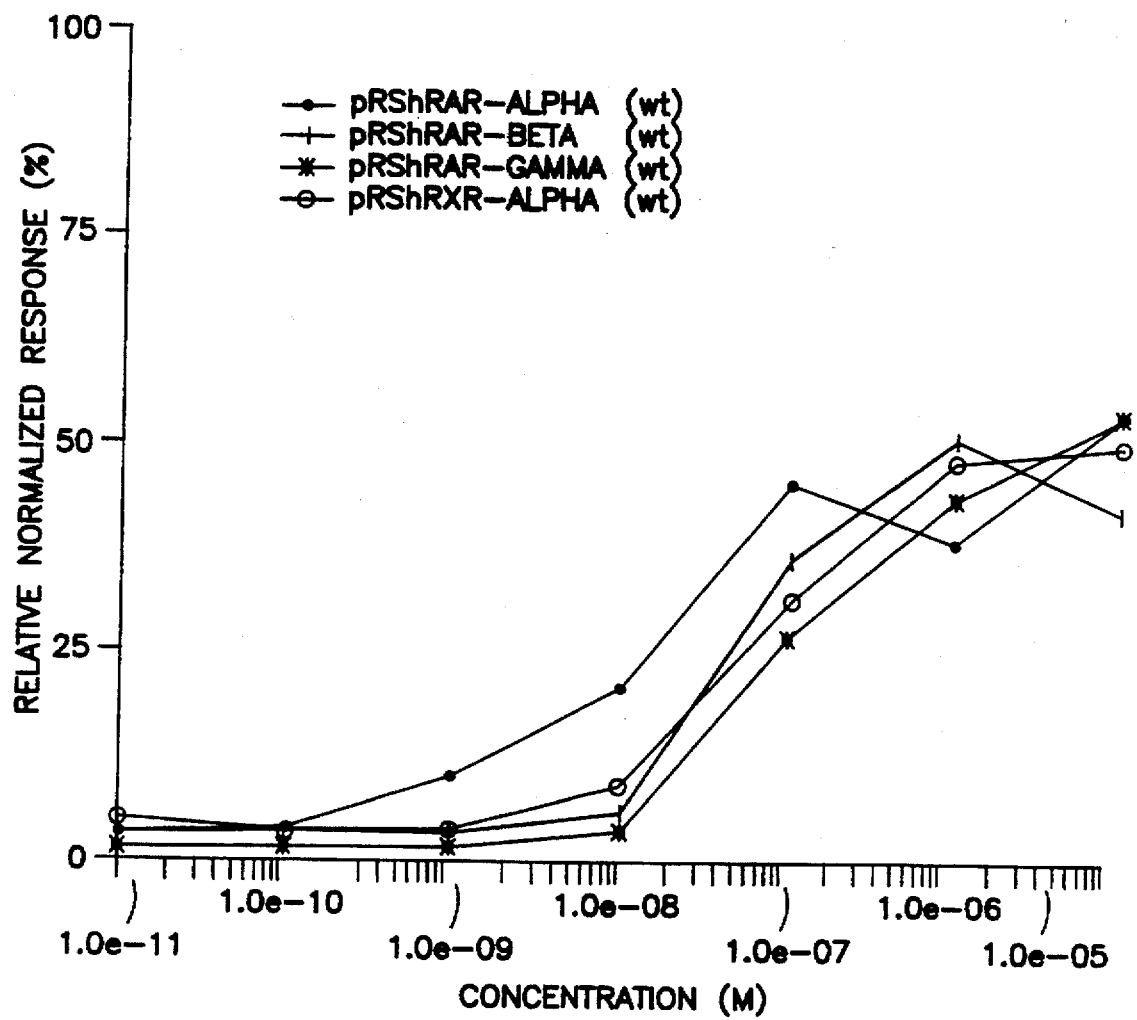
FIG. 4 is a dose response curve showing the response of RAR-α, RAR-β, RAR-γ, and RXR-α to increasing concentrations of the amide derivative referred to herein as Compound III.

FIG. 4 presents the results of a dose response study carried out with compound III (amide derivative) as the ligand for each of the receptors: RAR-α, RAR-β, RAR-γ, and RXR-α.

At very low concentrations of Compound III (i.e., concentrations below about $1 \times 10^{-9}$), each of the receptor subtypes is activated to approximately the same extent. Similarly, at concentrations above about $1 \times 10^{-7}$, each of the receptor subtypes is activated to approximately the same extent. However, at concentrations between about $1 \times 10^{-9}$ and $1 \times 10^{-7}$, the rank order potency is as follows:

RAR-α>RAR-β≈RXR-α>RAR-γ.

Thus, Compound III could be used for the treatment of a disease state which involves RAR-α, while perturbing pathways which are responsive to other retinoid receptors to a much lesser extent.

EXAMPLE V

Dose Response Curve For Compound IV

Figure 5:
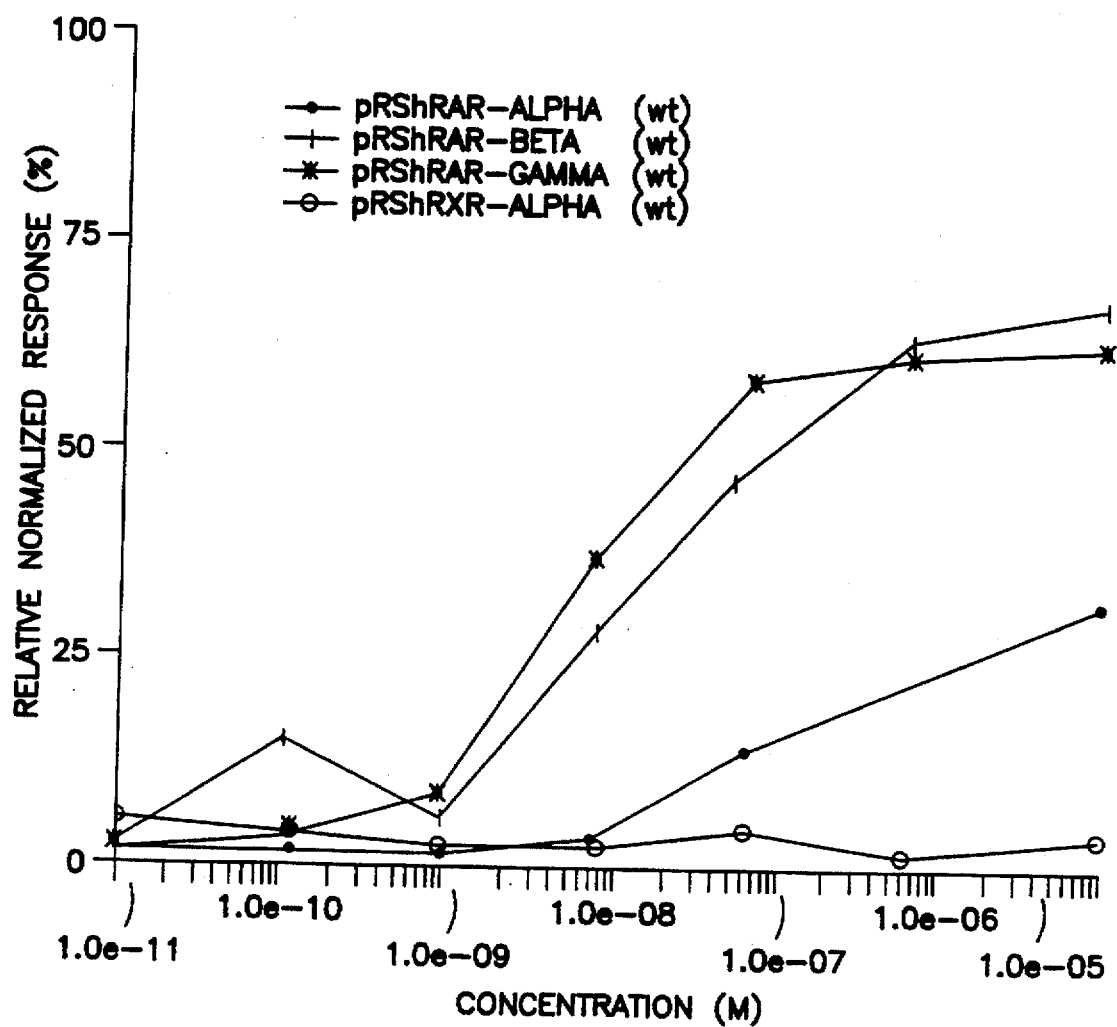
FIG. 5 is a dose response curve showing the response of RAR-α, RAR-β, RAR-γ, and RXR-α to increasing concentrations of the benzophenone derivative referred to herein as Compound IV.
Figure 5:
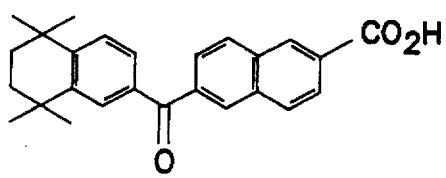

FIG. 5 presents the results of a dose response study carried out with compound IV (benzophenone derivative) as the ligand for each of the receptors: RAR-α, RAR-β, RAR-γ, and RXR-α.

At very low concentrations of Compound IV (i.e., concentrations below about $1 \times 10^{-9}$), each of the receptor subtypes is activated to approximately the same extent. However, at concentrations above about $1 \times 10^{-8}$, there is a readily discernible rank order potency as follows:

RAR-γ≈RAR-β>>>RAR-α≈RXR-α.

Thus, Compound IV could be used for the treatment of a disease state which involves RAR-γ and/or RAR-β, without perturbing pathways which are responsive to RAR-α or the retinoid X receptor.

While the invention has been described in detail with reference to certain preferred embodiments thereof, it will be understood that modifications and variations are within the spirit and scope of that which is described and claimed.

That which is claimed is:

1. A method for the treatment of a retinoid-responsive disease state in a subject, said method comprising administering to said subject an effective amount of a ligand which selectively interacts with the retinoid subtype associated with said retinoid-responsive disease state, to a significantly greater extent than with other retinoid subtypes.

2. A method according to claim 1 wherein said ligand which selectively interacts with the receptor subtype associated with said retinoid responsive disease state is selected from RAR-α selective ligands, RAR-β selective ligands, RAR-γ selective ligands, RXR-α selective ligands, RXR-β selective ligands, RXR-γ selective ligands.

3. A method according to claim 1 wherein said retinoid-responsive disease state is the result of translocation of a portion of a gene encoding a retinoid receptor and a portion of a second gene; wherein the expression of said second gene is not ordinarily subject to regulation by the retinoid which binds to said retinoid receptor.

4. A method according to claim 3 wherein said retinoid-responsive disease state is APL.

5. A method according to claim 1 wherein said retinoid-responsive disease state is a skin disorder.

* * * * *